United States Patent
Horita et al.

(10) Patent No.: US 7,935,078 B2
(45) Date of Patent: May 3, 2011

(54) MULTI-CHAMBERED SYRINGE

(75) Inventors: Taiji Horita, Ibaraki (JP); Ippei Matsumoto, Takaishi (JP)

(73) Assignee: Taisei Kako Co., Ltd., Osaka-shi (JP)

( * ) Notice: Subject to any disclaimer, the term of this patent is extended or adjusted under 35 U.S.C. 154(b) by 62 days.

(21) Appl. No.: 11/666,656

(22) PCT Filed: Jan. 27, 2006

(86) PCT No.: PCT/JP2006/301290
§ 371 (c)(1),
(2), (4) Date: May 1, 2007

(87) PCT Pub. No.: WO2006/082755
PCT Pub. Date: Aug. 10, 2006

(65) Prior Publication Data
US 2008/0215012 A1    Sep. 4, 2008

(30) Foreign Application Priority Data

Feb. 2, 2005 (JP) ................................ 2005-026270

(51) Int. Cl.
*A61M 37/00* (2006.01)
*A61M 5/00* (2006.01)
*A61M 5/315* (2006.01)

(52) U.S. Cl. .......... 604/82; 604/187; 604/191; 604/218; 604/222

(58) Field of Classification Search .............. 604/82–85, 604/89, 90, 187, 191, 218
See application file for complete search history.

(56) References Cited

U.S. PATENT DOCUMENTS 3,494,359 A * 2/1970 Zackheim ........................ 604/90

(Continued)

FOREIGN PATENT DOCUMENTS

| JP | 6-7446 | 1/1994 |
|---|---|---|
| JP | 8-280800 | 10/1996 |
| JP | 8-280807 | 10/1996 |
| JP | 9-628 | 1/1997 |
| JP | 9-216259 | 8/1997 |
| JP | 10-80485 | 3/1998 |
| JP | 11-169459 | 6/1999 |
| JP | 2004-65461 | 3/2004 |
| JP | 2004-141614 | 5/2004 |

OTHER PUBLICATIONS

Notification of Reason(s) for Refusal dated Nov. 16, 2010 with English Translation (4 pages).

*Primary Examiner* — Nicholas D Lucchesi
*Assistant Examiner* — William Carpenter
(74) *Attorney, Agent, or Firm* — Kratz, Quintos & Hanson, LLP (57) ABSTRACT

A multi-chamber syringe 10 which can be manufactured at a low-cost and high-productivity is provided. The syringe 10 includes a generally cylindrical barrel 12, a push member 14 and a plug 16, both of which are disposed to fit the inner side surface 12a of the barrel 12 and slidably on the inner side surface 12a. The plug 16 has a main surface 16a provided with a projection 34 having a top 34a which is eccentric to the main surface 16a. When the push member 14 slides in the direction indicated by Arrow A, the plug 16 comes under pressure from the side on the open end 18. When the projection 34 of the projection 16 makes contact with the choked end 20, the pressure from the side on the open end 18 acts to turn the plug 16 in the direction indicated by Arrow B. This causes a bending deformation in a main body 30 and flanges 32a, 32b of the plug 16, to form a first gap 38 and a second gap 40 between the inner side surface 12a of the barrel 12 and the plug 16.

3 Claims, 11 Drawing Sheets

U.S. PATENT DOCUMENTS

| | | | | |
|---|---|---|---|---|
| 4,437,858 A | * | 3/1984 | Ty | 604/90 |
| 4,496,344 A | * | 1/1985 | Kamstra | 604/90 |
| 4,613,326 A | * | 9/1986 | Szwarc | 604/89 |
| 4,929,230 A | * | 5/1990 | Pfleger | 604/90 |
| 4,997,423 A | * | 3/1991 | Okuda et al. | 604/230 |
| 5,605,542 A | | 2/1997 | Tanaka et al. | |
| 5,713,857 A | * | 2/1998 | Grimard et al. | 604/82 |
| 5,716,339 A | | 2/1998 | Tanaka et al. | |
| 5,720,731 A | * | 2/1998 | Aramata et al. | 604/191 |
| 5,817,056 A | | 10/1998 | Tanaka et al. | |
| 5,865,799 A | | 2/1999 | Tanaka et al. | |
| 2004/0097875 A1 | * | 5/2004 | Bae | 604/89 |

* cited by examiner

PRIOR ART

MULTI-CHAMBERED SYRINGE

RELATED APPLICATION AND CROSS-REFERENCE

This application claims the benefit of PCT/JP2006/301290 filed 27 Jan. 2006 and foreign priority towards Japanese Patent Application 2005-026270 filed 2 Feb. 2005.

TECHNICAL FIELD

The present invention relates to syringes, and more specifically to a multi-chamber syringe which includes a plug that partitions a barrel into two chambers each capable of storing a fluid.

BACKGROUND ART

Conventionally, as a prefilled syringe which is already filled with a medical substance, there is known a two-chamber syringe (so called dual syringe), as disclosed in Patent Document 1 for example, including a barrel which has two chambers each filled with a medical substance.

Figure 12:
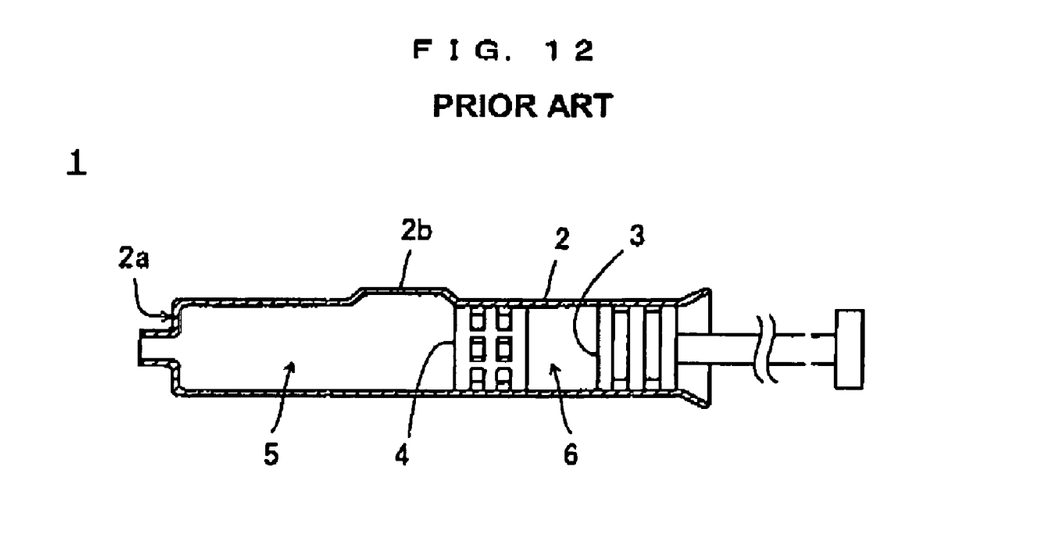
FIG. 12 A sectional schematic diagram showing a conventional syringe.

FIG. 12 shows a dual syringe 1 as disclosed in Patent Document 1. In the dual syringe 1, a push member 3 disposed in a generally cylindrical barrel 2 is moved toward a choked end 2a, to apply pressure to a plug 4 which partitions the inside space of the barrel 2. When the pressurized plug 4 moves toward the choked end 2a, the medical substance filled in a space 5 between the plug 4 and the choked end 2a is injected from an injection hole formed in the choked end 2a. Then, when the plug 4 reaches a recess (where the inner diameter is increased) 2b formed in an inner side surface of the barrel 2, the medical substance stored in a space 6 between the push member 3 and the plug 4 flows through a bypass formed between the plug 4 and the recess 2b, into the space 5.

Patent Document 1: JP-A 6-7446

DISCLOSURE OF THE INVENTION

Problems to be Solved by the Invention

However, in the dual syringe 1, the barrel 2 formed with the recess 2b is essential. The barrel 2 as described may be made of synthetic resin, and if formed by injection molding for example, a special metal mold must be prepared. This poses a problem of high cost, which leads to a high cost of the dual syringe 1. Further, the barrel 2 formed with the recess 2b has another problem of low product yield and low productivity due to burr formation when molding the recess 2b with synthetic resin, or due to shape inconsistency, etc. of the recess 2b if it is made of glass.

Therefore, a primary object of the present invention is to provide a multi-chamber syringe which can be manufactured at a low-cost and high-productivity.

Means for Solving the Problem

According to an aspect of the present invention, there is provided a multi-chamber syringe which includes: a barrel having an open end and a choked end, the choked end having an injection hole; a push member disposed to fit an inner side surface of the barrel and slidably on the inner side surface; and an elastic plug disposed more closely to the choked end than the push member, to fit the inner side surface and slidably on the inner side surface. The plug partitions an inside space of the barrel into two chambers each capable of storing a fluid.

The syringe further includes: a first projection with an eccentric top, provided on the plug's main surface on a choked end side; and a flow path made between the inner side surface and the plug. Application of a pressure from an open end side to the plug, with the first projection contacting with the choked end, makes a first gap opening on the open end side and communicating with the flow path, and a second gap opening on the choked end side and communicating with the flow path, between the inner side surface and the plug.

According to the present invention, when the plug receives pressure from the open end side while the first projection contacts the choked end, the pressure from the open end side acts in the direction to turn the plug, causing the flexible plug to deform thereby making a first gap and the second gap, between the inner side surface of the barrel and the plug. Thus, the fluid stored in a space between the push member and the plug flows through the first gap, the flow path and the second gap in this order, and is injected from the injection hole. Therefore, the present invention makes possible to obtain multi-chamber syringes at a low cost and high productivity, using a simple barrel which is not formed with a recess for example.

Preferably, the first projection has a slanted surface slanted with respect to the plug's main surface on the choked end side, and does not to make contact with the inner side surface, and the slanted surface is formed with a groove for connecting the second gap with the injection hole. In this case, when the pressure from the open end side acts in the direction to turn the plug, the deformed plug tilts in the barrel, bringing the slanted surface of the first projection into contact with the choked end. The fluid from the second gap then flows through the groove formed in the slanted surface of the first projection, and is injected from the injection hole. As described, by tilting the plug within the barrel, the first gap and the second gap can be opened widely, enabling to inject the fluid which is stored in the space between the push member and the plug efficiently from the injection hole. Further, mutual contact between the choked end and the slanted surface of the first projection enables to hold the tilted plug stably in the barrel.

Further preferably, the syringe further includes a second projection provided on the plug's another main surface on the open end side. The second projection is eccentric in an opposite direction as to the first projection, on a plane parallel to the plug's main surface, and does not make contact with the inner side surface. In this case, the pressure from the open end side is received by the second projection, which helps the pressure from the open end side act in the direction to turn the plug, enabling to tilt the plug easily in the barrel.

The above-described object, other objects, characteristics, aspects and advantages of the present invention will become clearer from the following detailed description of embodiments to be made with reference to the attached drawings.

BRIEF DESCRIPTION OF THE DRAWINGS

FIG. 6 Shows the plug in FIG. 5: FIG. 6(a) is a front view of the plug in FIG. 5 whereas FIG. 6(b) is a side view of the plug in FIG. 5.

FIG. 7 Shows the plug in FIG. 5: FIG. 7(a) is a plan view of the plug in FIG. 5 whereas FIG. 7(b) is a bottom view of the plug in FIG. 5.

FIG. 10 Shows the plug in FIG. 9: FIG. 10(a) is a front view of the plug in FIG. 9 whereas FIG. 10(b) is a side view of the plug in FIG. 9.

LEGEND

| | |
|---|---|
| 10, 10a | Syringe |
| 12 | Barrel |
| 14 | Push member |
| 16, 100, 200 | Plugs |
| 16a, 100a, 100b | Main surfaces |
| 18 | Open end |
| 20 | Choked end |
| 20a | Injection portion |
| 20b | Injection hole |
| 26a, 26b, 26c, 32a, 32b, 104a, 104b | Flanges |
| 34, 106, 108, 202 | Projections |
| 34a, 106a, 108a, 202a | Tops |
| 36, 110 | Flow paths |
| 38, 112 | First gaps |
| 40, 114 | Second gaps |
| 106b, 106c, 108b, 108c, 202b, 202c | Slanted surfaces |
| 106d, 202d | Grooves |
| L1, L2 | Medical substances |

BEST MODE FOR CARRYING OUT THE INVENTION

Hereinafter, embodiments of the present invention will be described with reference to the drawings.

The description will cover cases where the present invention is applied to a 2-chamber syringe (dual syringe).

Figure 1:
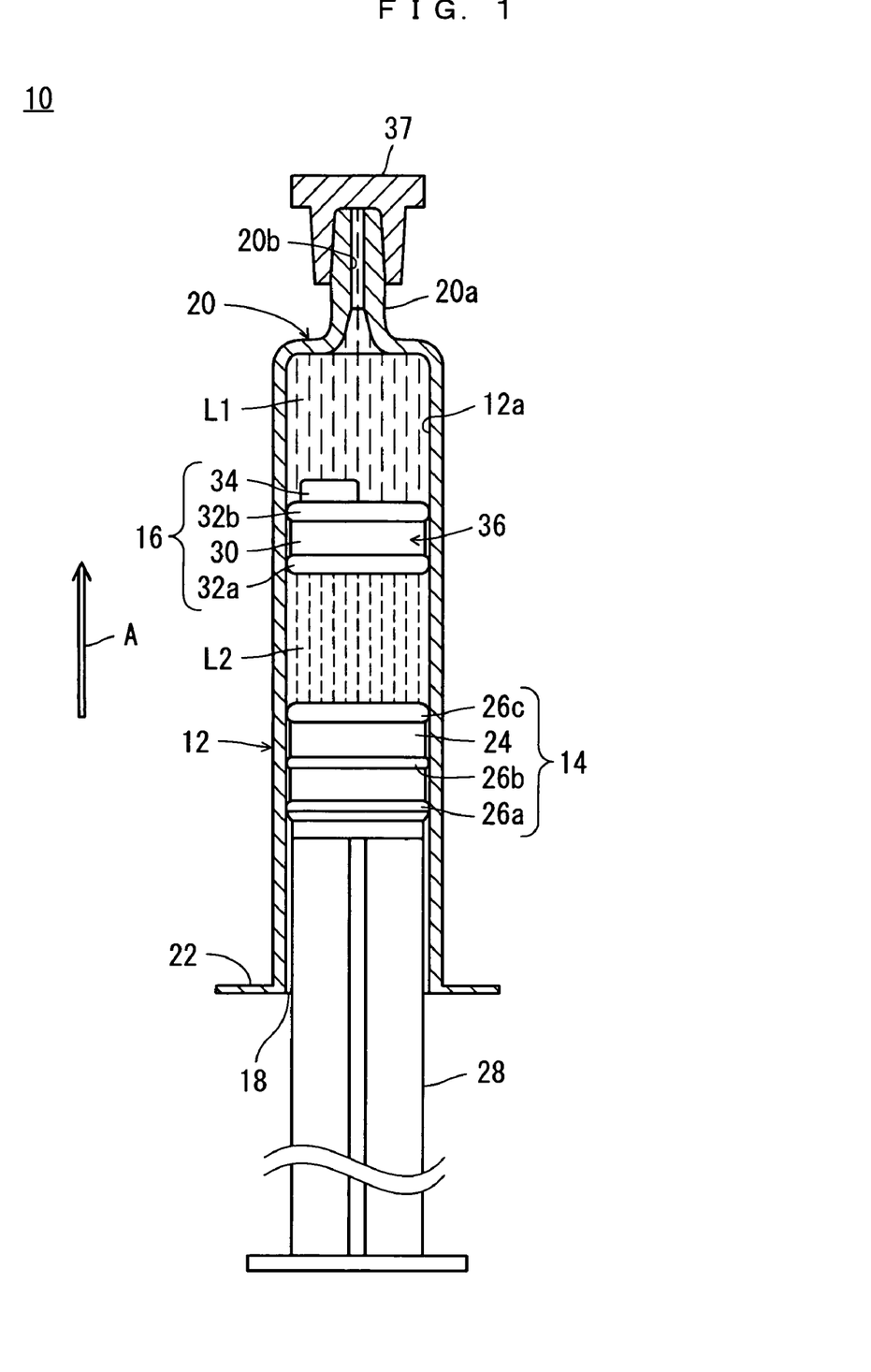
FIG. 1 A sectional schematic diagram showing an example of the syringe according to the present invention.

Referring to FIG. 1, a syringe 10 as an embodiment of the present invention includes a generally cylindrical barrel 12 having a generally consistent inner diameter, as well as a push member 14 and a plug 16 each fitted to an inner side surface 12a of the barrel 12 and slidable on the inner side surface 12a.

The barrel 12 has an open end 18 and a choked end 20. At a substantial center of the choked end 20, there is formed an injection portion 20a to extend axially (in the direction indicated by Arrow A) of the barrel 12. The injection portion 20a is provided with an injection hole 20b. Further, the open end 18 of the barrel 12 is provided with a flange 22. The barrel 12 as described can be obtained easily from injection molding process of a synthetic resin such as polypropylene, cyclic olefin, cyclic polyolefin and polymethylpentene, using a common mold.

The push member 14, which is an elastic member made of a flexible material such as butyl rubber, has a generally columnar main body 24 and flanges 26a-26c which are provided circumferentially on a side surface of the main body 24. The flanges 26a-26c have an outer diameter which is greater than the inner diameter of the barrel 12 within a range to allow the push member 14 to slide on an inner side surface 12a.

Therefore, the push member 14 has a tight contact with the inner side surface 12a at its flanges 26a-26c. The push member 14 has a main surface on a side of the open end 18. A pushing rod 28 is attached to the main surface, extending out of the barrel 12.

The plug 16 is disposed between the push member 14 and the choked end 20, partitioning the space in the barrel 12. Thus, the barrel 12 has a chamber between the plug 16 and the choked end 20, and another chamber between the push member 14 and the plug 16.

Figure 2:
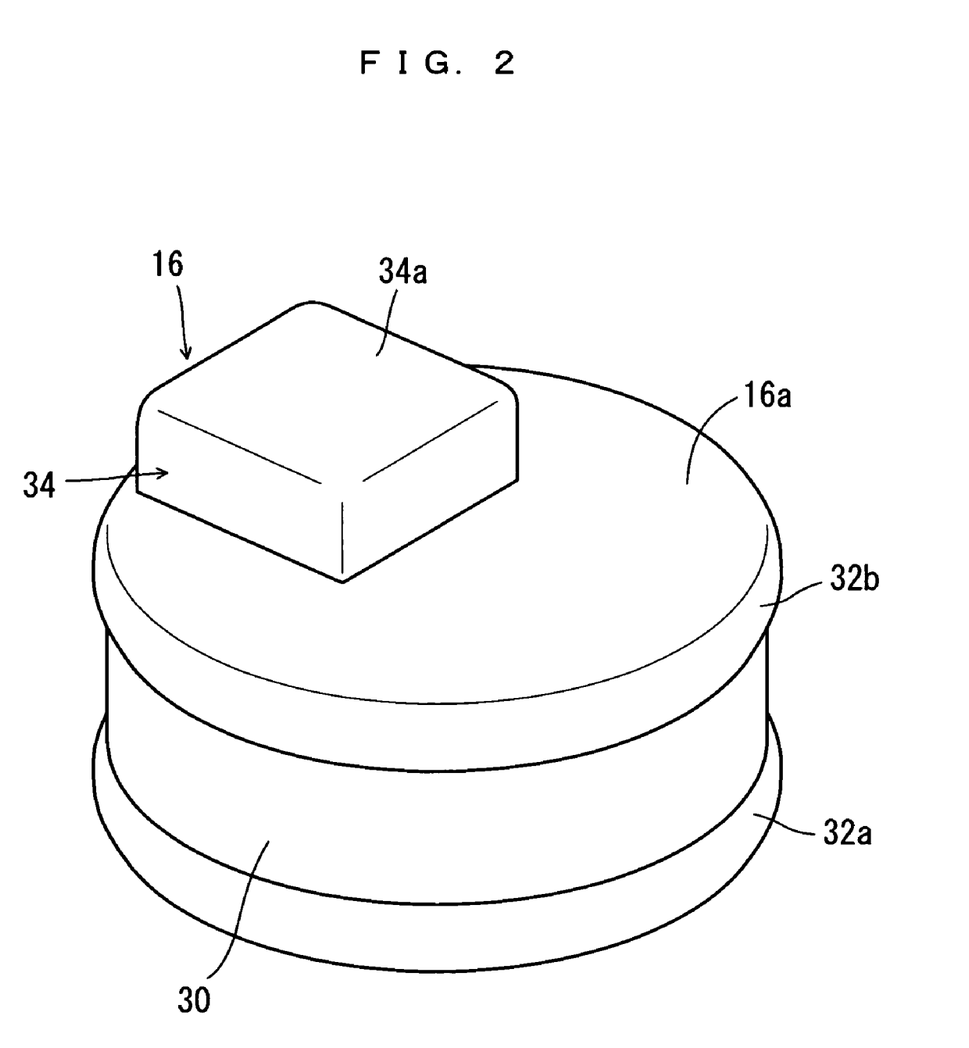
FIG. 2 A perspective view showing a plug used in the syringe in FIG. 1.

Referring also to FIG. 2, the plug 16 is an elastic member made of a flexible material such as butyl rubber. The plug 16 has: a generally columnar main body 30; a flange 32a provided on a side surface of the main body 30, at an end closer to the open end 18; a flange 32b provided on the side surface of the main body 30, at an end closer to the choked end 20; and a projection 34 provided on a main surface 16a of the plug 16 which is a surface facing the choked end 20. In this embodiment, the projection 34 represents the first projection.

The main body 30 is generally columnar, and has an outer diameter which is smaller than the inner diameter of the barrel 12. The flanges 32a, 32b have an outer diameter which is greater than the inner diameter of the barrel 12 within a range to allow the plug 16 to slide on the inner side surface 12a. Therefore, the plug 16 has a tight contact with the inner side surface 12a at its flanges 32a, 32b. A flow path 36 is provided between the flanges 32a, 32b and between the main body 30 of the plug 16 and the inner side surface 12a.

The projection 34 is formed on the main surface 16a, substantially as a quadrangular prism, off the center of the substantially circular main surface 16a, more closely to the inner side surface 12a of the barrel 12. In other words, the projection 34 is provided on the main surface 16a so that its top 34a is eccentric to the main surface 16a.

In the syringe 10 as described, the space in the barrel 12 between the plug 16 and the choked end 20 is prefilled with a liquid medical substance L1, whereas the space in the barrel 12 between the push member 14 and the plug 16 is prefilled with another kind of liquid medical substance L2. The syringe 10, which is a prefilled syringe, is used as an injector for example, when an injection needle is attached to the injection portion 20a. As shown in FIG. 1, a seal member 37 is attached to the injection portion 20a in order to prevent the medical substance from leaking out from the injection hole 20b, before being used. When used, the seal member 37 is manually removed, and the pushing rod 28 is pushed in the direction indicated by Arrow A, whereby the medical substances L1, L2 are injected sequentially from the injection hole 20b.

Figure 3:
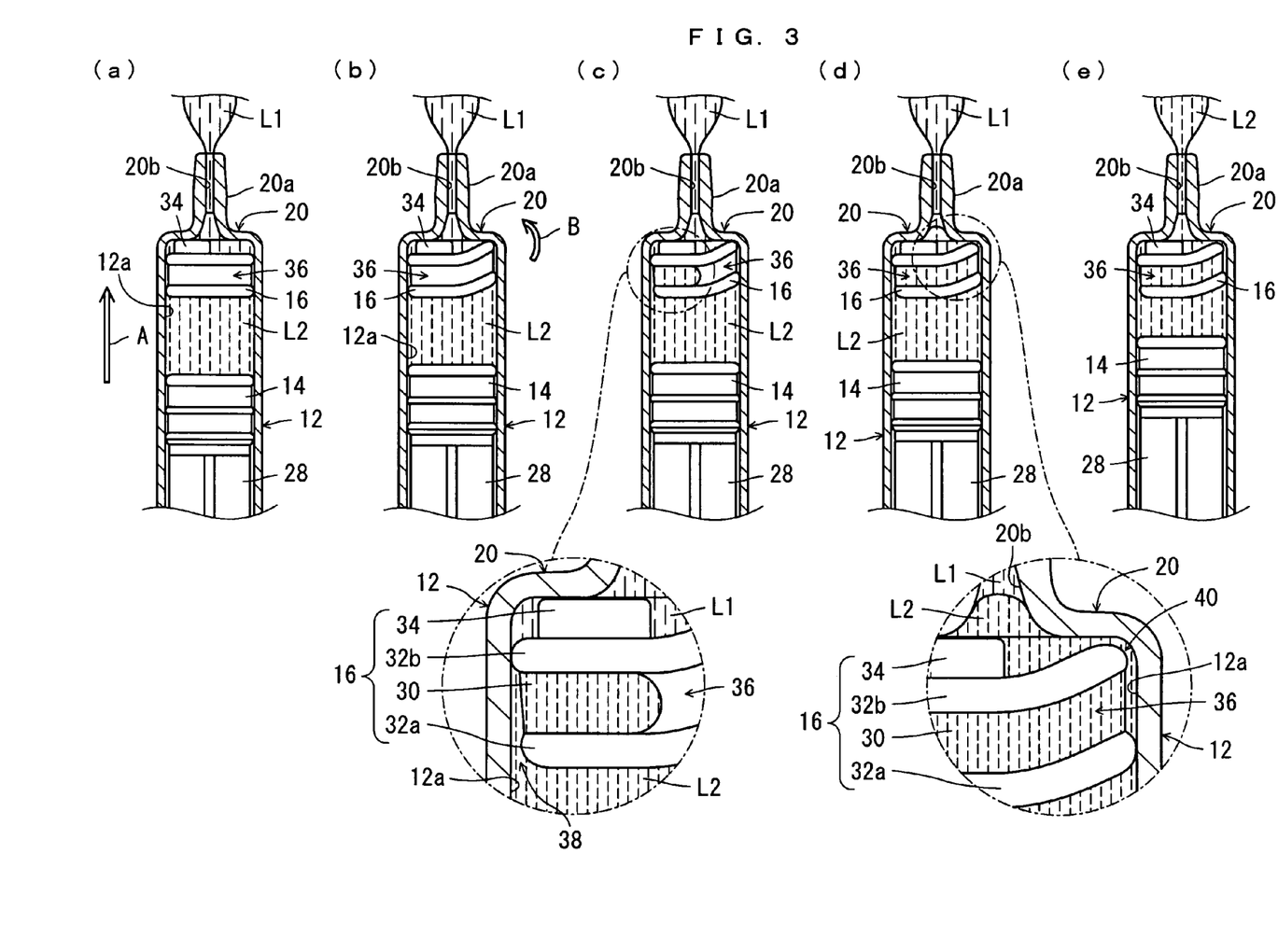
FIG. 3 A sectional schematic diagram showing how injection is made by the syringe in FIG. 1.

Next, reference will be made to FIG. 3(a) through FIG. 3(e), to describe how the medical substances L1, L2 are injected, according to the syringe 10.

First, the seal member 37 is removed. When the pushing rod 28 is pushed in the direction indicated by Arrow A, the push member 14 slides on the inner side surface 12a in the direction of Arrow A, whereby pressure is applied from the side on the open end 18 to the plug 16 via the medical substance L2. Accordingly, as shown in FIG. 3(a), the plug 16 slides on the inner side surface 12a in the direction of Arrow A, to inject the medical substance L1 from the injection hole 20b. When the top 34a of the projection 34 (See FIG. 2) makes contact with the choked end 20, the plug 16 stops sliding.

Then, as shown in FIG. 3(b), with the top 34a of the projection 34 (See FIG. 2) contacted with the choked end 20, the plug 16 further receives pressure from the side on the open end 18, whereby a portion of the main body 30 and of the flanges 32a, 32b of the plug 16 which has some space toward the choked end 20 is pushed toward the choked end 20. Thus, the pressure from the side on the open end 18 acts in a direction (indicated by Arrow B) to turn the plug 16, deforming the main body 30 and the flanges 32a, 32b to bend.

Subsequently, as shown in FIG. 3(c), when the plug 16 further receives pressure from the side on the open end 18, part of the flange 32a closest to the push member 14 comes off the inner side surface 12a, i.e. opens up to the side on the open end 18, to make a first gap 38 leading to the flow path 36. Thus, the medical substance L2 in the space between the push member 14 and the plug 16 flows through the first gap 38 into the flow path 36.

Then, as shown in FIG. 3(d), the medical substance L2 which flows into the flow path 36 presses the flange 32b near the corner between the inner side surface 12a and the choked end 20, thus causing the flange 32b to come off the inner side surface 12a, i.e. to open up to the side on the choked end 20, to make a second gap 40 leading to the flow path 36. Thereafter, as shown in FIG. 3(e), the medical substance L2 passes through the second gap 40, flows into the injection hole 20b of the injection portion 20a, and then is injected from the injection hole 20b.

According to the syringe 10 as the above, the medical substance L2 stored in the space between the push member 14 and the plug 16 passes the first gap 38, the flow path 36 and the second gap 40 in this order, and then is injected from the injection hole 20b. Therefore, it is possible to obtain the syringe 10, using a simple barrel 12 which has a generally consistent inner diameter, at a low cost and high productivity.

Further, the plug 16 fits the inner side surface 12a of the barrel 12, at the flanges 32a, 32b which are larger than the inner diameter of the barrel. This prevents such a problem that the plug 16 will be tilted within the barrel 12 by the pressure from the side on the open end 18 before the projection 34 makes contact with the choked end 20. In other words, this prevents the medical substance L1 and the medical substance L2 from mixing with each other in the barrel 12.

Next, description will be made for a syringe 10a which is another embodiment of the present invention.

Figure 4:
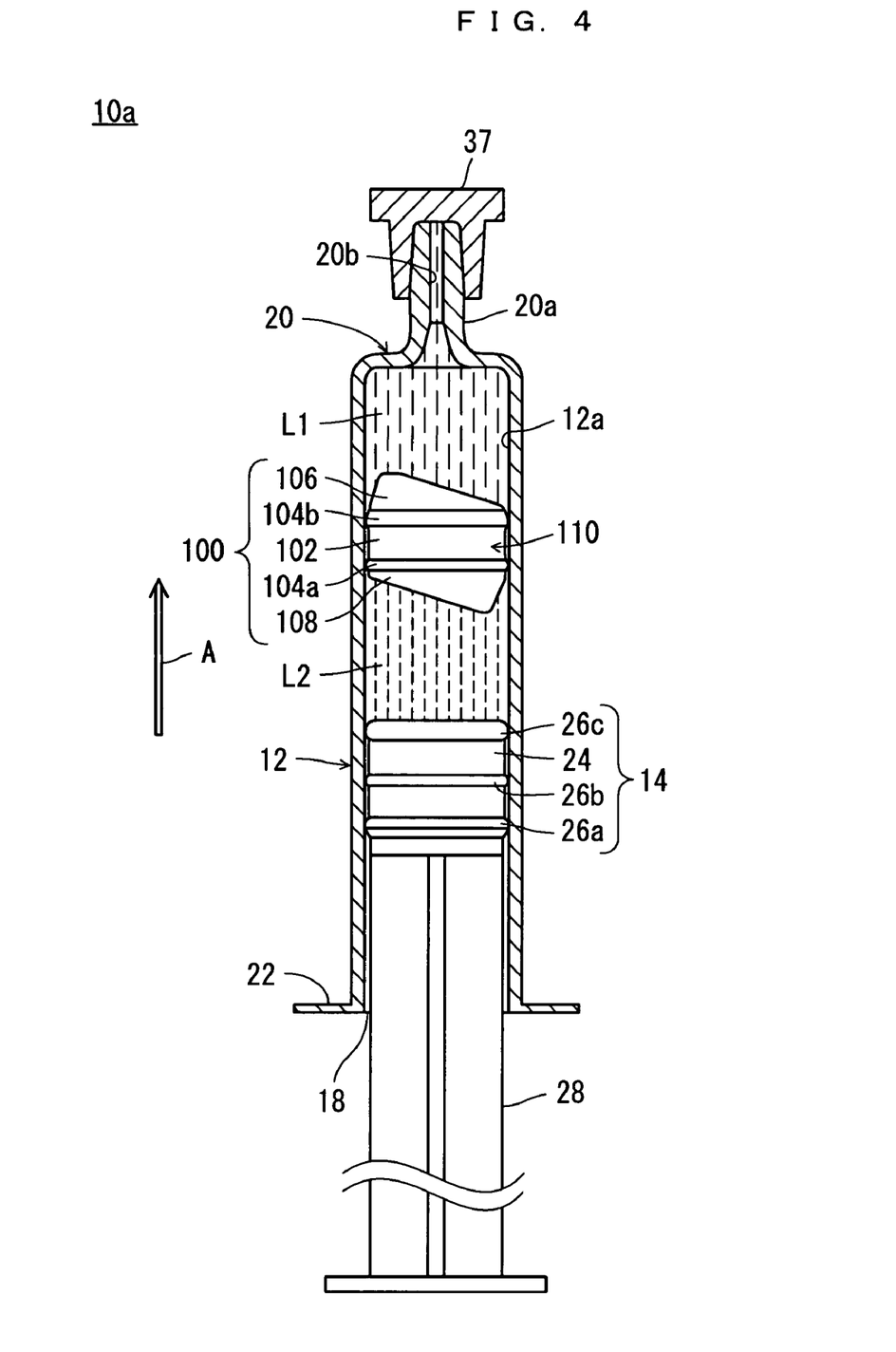
FIG. 4 A sectional schematic diagram showing another example of the syringe according to the present invention.

In the syringe 10a shown in FIG. 4, the plug 16 used in the above-described syringe 10 is replaced by a plug 100. Other aspects are identical with those of the syringe 10, so the description will not be repeated.

Referring to FIG. 4 through FIG. 7, the plug 100 is an elastic member made of a flexible material such as butyl rubber. The plug 100 has: a generally columnar main body 102, a flange 104a provided on a side surface of the main body 102, at an end facing the open end 18; a flange 104b provided on the side surface of the main body 102, at an end facing the choked end 20; a projection 106 provided on a main surface 100a which is a surface of the plug 100 facing the choked end 20; and a projection 108 provided on a main surface 100b which is a surface of the plug 100 facing the open end 18. In the present embodiment, the projection 106 represents the first projection, and the projection 108 represents the second projection.

The flanges 104a, 104b have an outer diameter which is greater than the inner diameter of the barrel 12 within a range to allow the plug 100 to slide on the inner side surface 12a. Therefore, the plug 100 has a tight contact with the inner side surface 12a at its flanges 104a, 104b. A flow path 110 is provided between the flanges 104a, 104b and between the main body 102 of the plug 100 and the inner side surface 12a.

Figure 5:
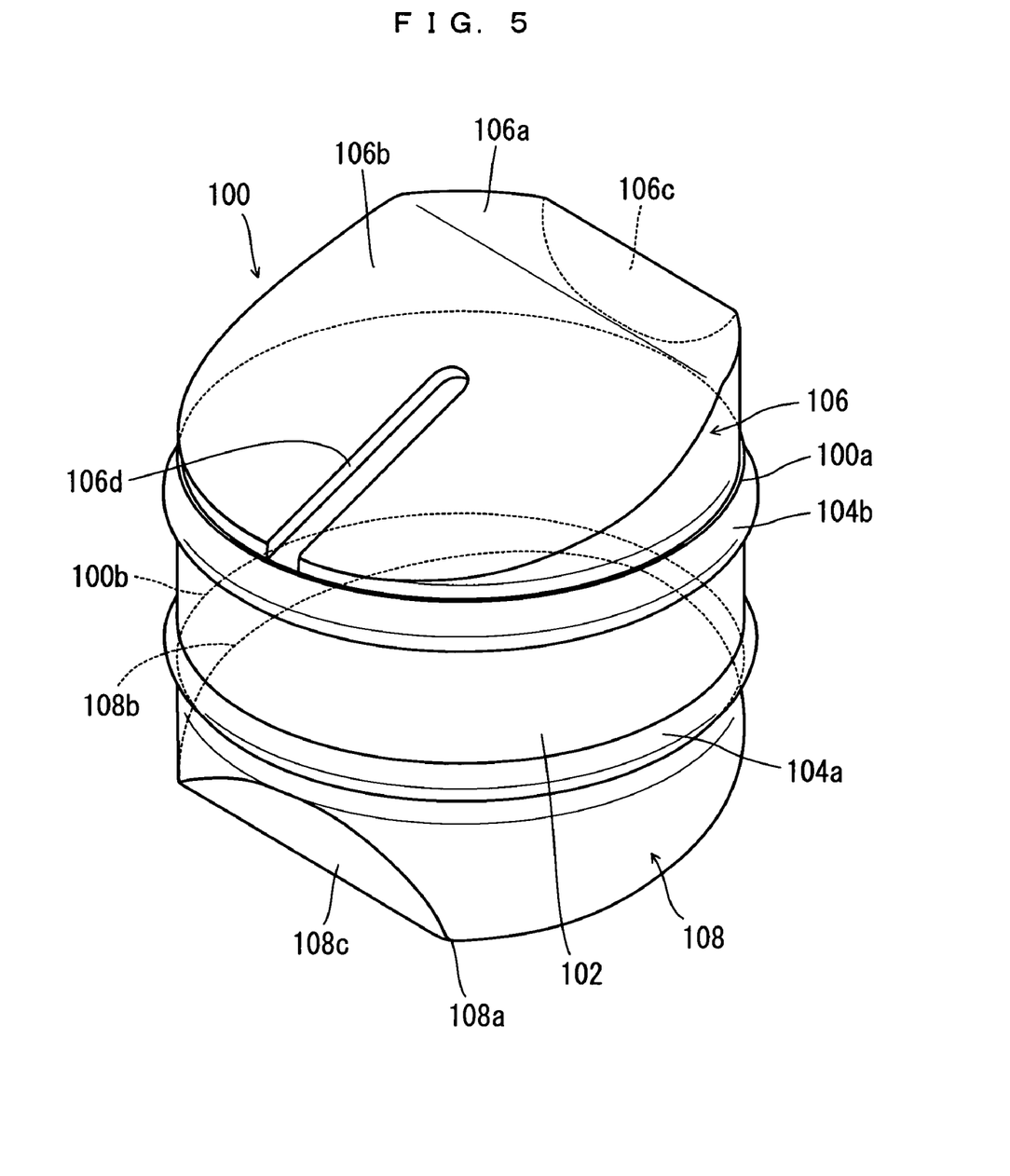
FIG. 5 A perspective view showing a plug used in the syringe in FIG. 4.
Figure 6:
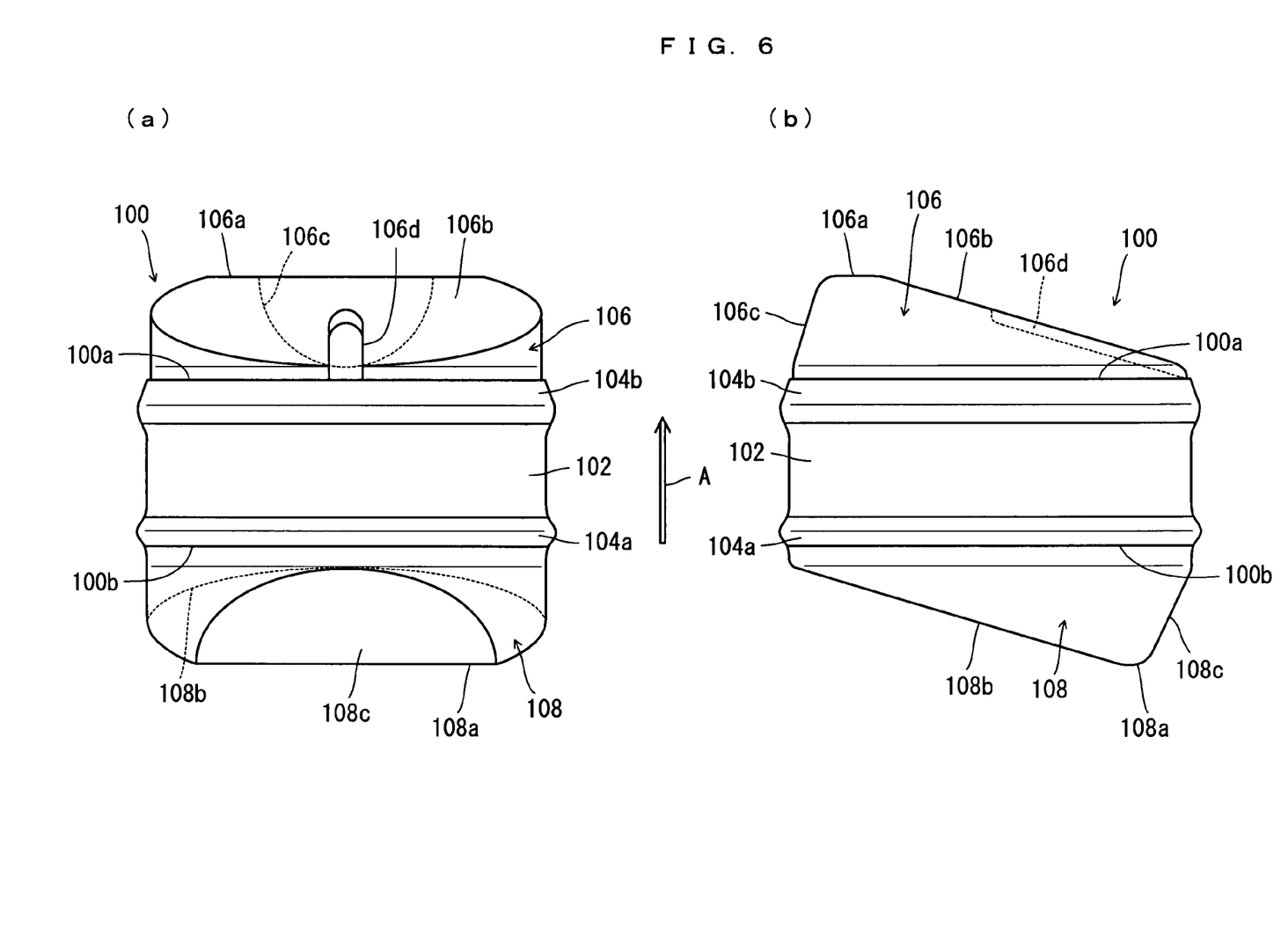
Figure 7:
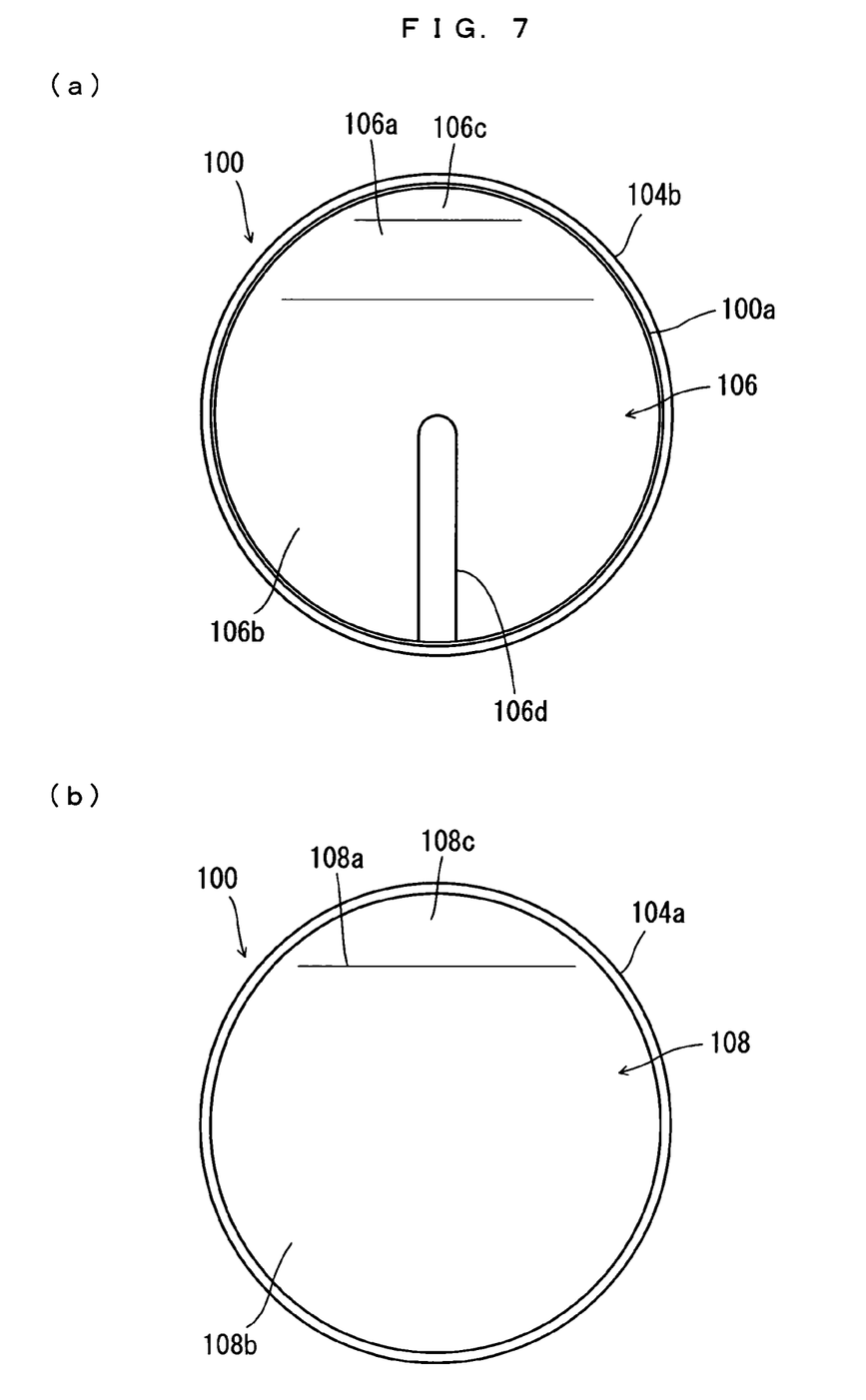

As shown in FIG. 5 through FIG. 7, the projection 106 has a top 106a which is parallel to the main surface 100a, and slanted surfaces 106b, 106c sandwiching the top 106a. The projection 106 is provided on the main surface 100a so that the top 106a is eccentric with respect to the main surface 100a. Further, the projection 106 makes no contact with the inner side surface 12a, being smaller than the inner diameter of the barrel 12. The slanted surface 106b is slanted to the main surface 100a by 17° for example. The slanted surface 106c is slanted to the main surface 100a by 73° for example. Note that the slanted surface 106b is formed with a groove 106d extending from the center of the projection 106 to a circumferential edge of the main surface 100a, for connecting the second gap 114 (to be described later) with the injection hole 20b.

The projection 108 has a top 108a, and slanted surfaces 108b, 108c sandwiching the top 108a. As understood from FIG. 6(b), the top 108a of the projection 108 is located perpendicularly to the direction of Arrow A, and away from the top 106a of the projection 106. In other words, the projection 108 is provided on the main surface 100b, in parallel to the main surfaces 100a, 100b and in the opposite eccentric direction from the direction of eccentricity of the projection 106. Further, the projection 108 makes no contact with the inner side surface 12a, being smaller than the inner diameter of the barrel 12. The slanted surface 108b is slanted to the main surface 100b by 17° for example. The slanted surface 108c is slanted to the main surface 100b by 65° for example.

Figure 8:
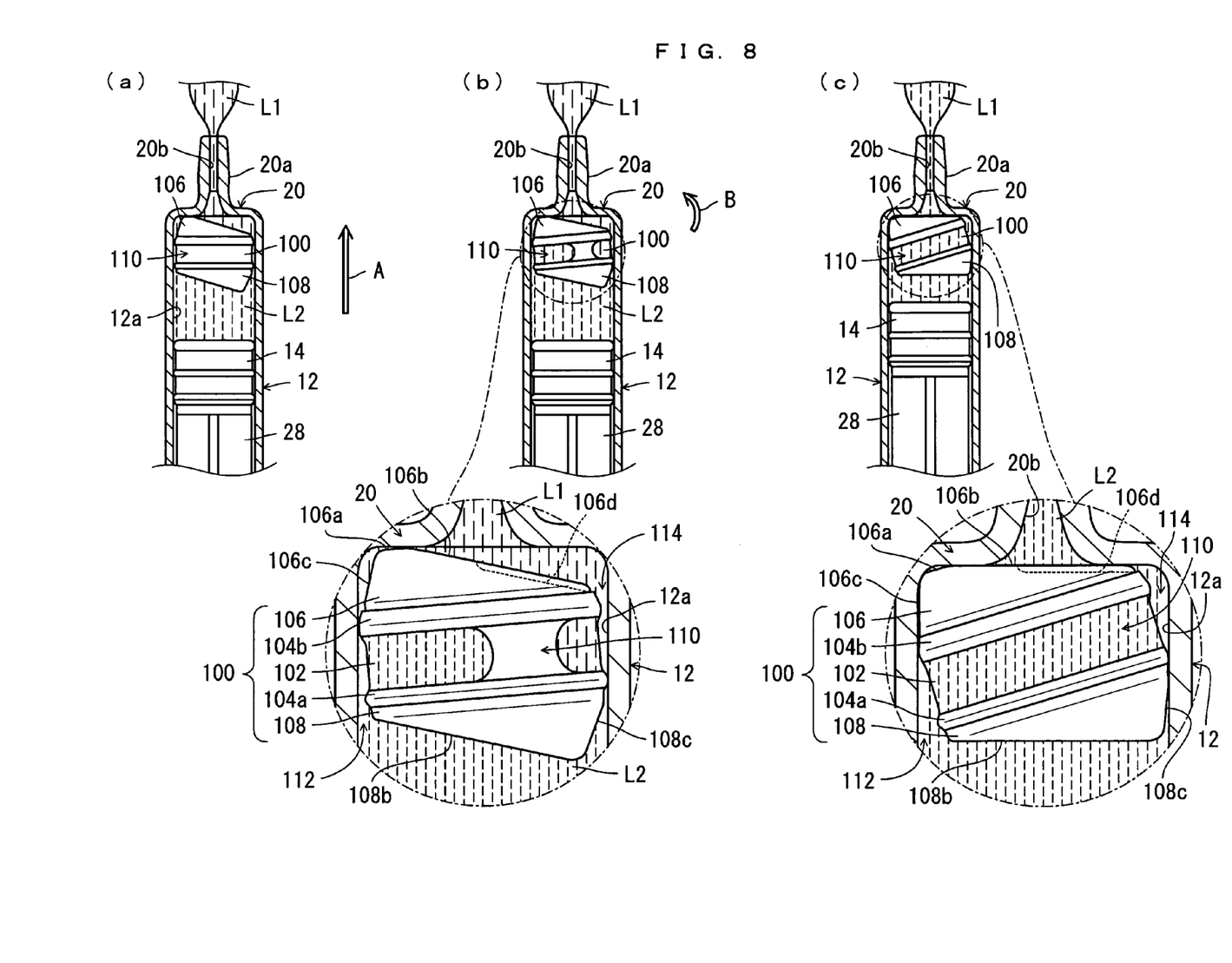
FIG. 8 A sectional schematic diagram showing how injection is made by the syringe in FIG. 4.

Next, reference will be made to FIG. 8(a) through FIG. 8(c), to describe how the medical substances L1, L2 are injected, according to the syringe 10a which uses the plug 100 as described above.

First, when the pushing rod 28 is pushed in the direction indicated by Arrow A, the push member 14 slides on the inner side surface 12a in the direction of Arrow A, whereby pressure from the side on the open end 18 is applied to the plug 100 via the medical substance L2. Accordingly, as shown in FIG. 8(a), the plug 100 slides on the inner side surface 12a in the direction of Arrow A, to inject the medical substance L1 from the injection hole 20b. When the top 106a of the projection 106 makes contact with the choked end 20, the plug 100 stops sliding.

Then, as shown in FIG. 8(b), with the top 106a of the projection 106 already having made contact with the choked end 20, the plug 100 still receives the pressure from the side on the open end 18, mainly on the slanted surface 108b of the projection 108. Thus, the pressure from the side on the open end 18 acts in the direction indicated by Arrow B. As a result, the flange 104a is pressed against the inner side surface 12a, and is deformed near an end of the slanted surface 108c which is an end closer to the main surface 100b (See FIG. 5). Meanwhile, the flange 104b is pressed against the inner side surface 12a, and is deformed near an end of the slanted surface 106c which is an end closer to the main surface 100a (See FIG. 5). Then, the plug 100 turns in the direction of Arrow B, to begin to tilt in the barrel 12, making the flange 104a come off the inner side surface 12a near an end of the slanted surface 108b which is an end closer to the main surface 100b (See FIG. 5), while making the flange 104b come off the inner side surface 12a near an end of the slanted surface 106b which is an end closer to the main surface 10a (See FIG. 5). In other words, a first gap 112 is made which opens to the side on the open end 18 and communicates with the flow path 110, and a second gap 114 is made which opens to the side on the choked end 20 and communicates with the flow path 110. Thus, the medical substance L2 in the space between the push member 14 and the plug 100 flows through the first gap 112 into the flow path 110.

Subsequently, as shown in FIG. 8(c), the slanted surface 108b of the projection 108 further receives pressure from the side on the open end 18, causing the plug 100 to tilt further in the barrel 12. This brings the slanted surface 106*b* of the projection 106 into contact with the choked end 20, while bringing the slanted surface 106*c* of the projection 106 and the slanted surface 108*c* of the projection 108 into contact with the inner side surface 12*a*. Thereafter, the medical substance L2 which has passed through the second gap 114 flows through the groove 106*d*, into the injection hole 20*b* of the injection portion 20*a*, and is injected from the injection hole 20*b*.

According to the syringe 10*a* as described, it is possible to open the first gap 112 and the second gap 114 widely by tilting the plug 100 in the barrel 12, and to inject the medical substance L2 in the space between the push member 14 and the plug 100 efficiently from the injection hole 20*b*.

Further, it is possible to retain the tilted plug 100 stably in the barrel 12, by the contact of the slanted surface 106*b* of the projection 106 with the choked end 20 as well as by the contact of the slanted surface 106*c* of the projection 106 and the slanted surface 108*c* of the projection 108 with the inner side surface 12*a*.

Further, the pressure from the side on the open end 18 is received mainly by the slanted surface 108*b* of the projection 108. Thus, the pressure from the side on the open end 18 acts easily in the direction of Arrow B [See FIG. 8(*b*)], enabling to tilt the plug 100 easily in the barrel 12.

It should be noted that the slanted surface 108*b* of the projection 108 may also be formed with a groove which is like the groove 106*d*. This permits the plug 100 to be disposed in the opposite direction in the barrel 12, with the projection 108 facing the choked end 20, eliminating such a mistake that the plug 100 is placed in the wrong direction when disposing the plug 100 in the barrel 12.

Further, the shape of the first projection is not limited to the shape of the projection 106.

Figure 9:
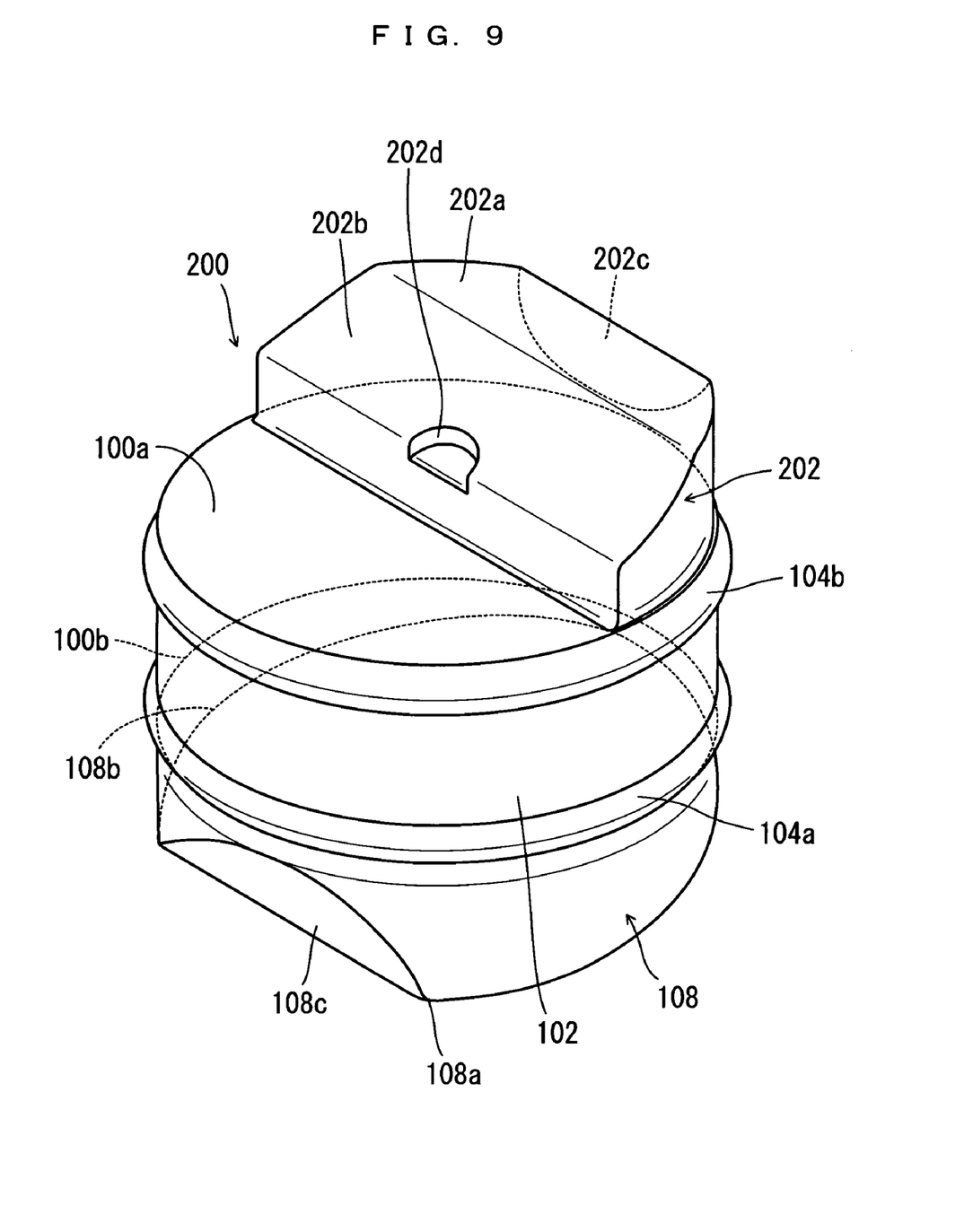
FIG. 9 A perspective view showing another example of the plug.
Figure 10:
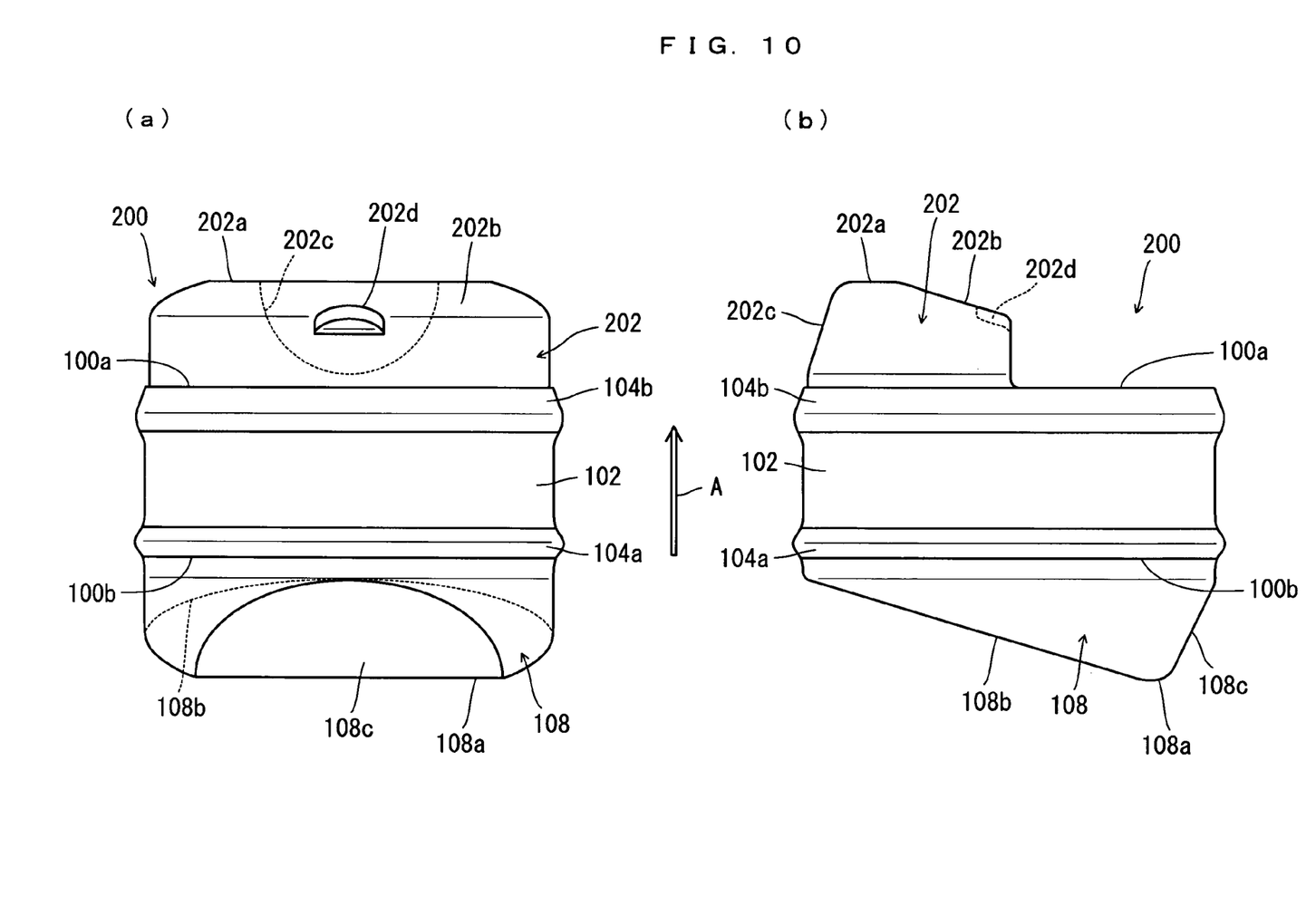
Figure 11:
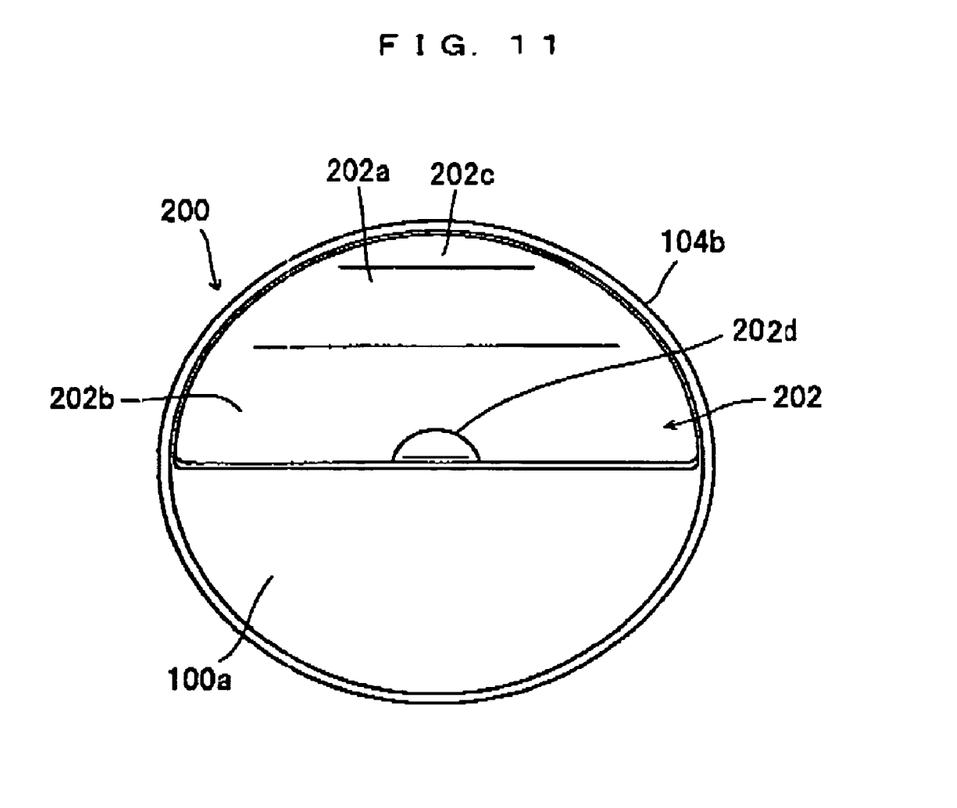
FIG. 11 A plan view of the plug in FIG. 9.

Now, reference will be made to FIG. 9 through FIG. 11 to describe a plug 200. The plug 200 has a main surface 100*a* provided with a projection 202, which is the projection 106 (See FIG. 5 through FIG. 7) except that the slanted surface 106*b* is cut substantially at a center of the main surface 100*a* perpendicularly to the main surface 100*a*. The difference between the plug 100 and the plug 200 is only the difference between the projection 106 and the projection 202, and so repetitive description will not be given here.

The projection 202 has a top 202*a* which is parallel to the main surface 100*a*, and slanted surfaces 202*b*, 202*c* sandwiching the top 202*a*. The top 202*a* is provided the same way as is the top 106*a* of the projection 106, and so is the slanted surface 202*c* as the slanted surface 106*c* of the projection 106. As shown in FIG. 11, the slanted surface 202*b* is generally trapezoidal as in a plan view. The slanted surface 202*b* is formed with a groove 202*d* for connecting the second gap 114 [See FIG. 8(*c*)] with the injection hole 20*b* (See FIG. 4). The groove 202*d* has a width which is approximately two times the width of the groove 106*d* [See FIG. 7(*a*)] of the projection 106. As understood from FIG. 11, the projection 202 is generally semicircular as in a plan view, and is provided on the main surface 100*a* to cover approximately a half of the main surface 100*a*.

When using the plug 200 as the above, the slanted surface 202*b* makes contact with the choked end 20 when the plug 200, which is contacting with the choked end 20 (See FIG. 4) of the barrel 12 at the top 202*a*, tilts. At this point, there is a space between the choked end 20 and a portion made by the main surface 100*a* of the plug 200 plus the projection 202 of the plug 200. The medical substance L2 which comes through the second gap 114 [See FIG. 8(*c*)] flows into the space. With this arrangement, it is possible to allow the medical substance L2 to flow swiftly from the groove 202*d* of the slanted surface 202*b* and the space, into the injection hole 20*b* of the barrel 12, enabling to inject the medical substance L2 efficiently from the injection hole 20*b*.

It should be noted that the area of the slanted surface 202*b* of the projection 202, and accordingly the volume of the space made by the main surface 100*a* of the plug 200, the projection 202 of the plug 200 and the choked end 20 are discretional.

Besides the shapes of the projections 106, 202, the shape of the first projection is discretional as long as it is easy to form and does not trap bubbles easily at the first projection if a gaseous substance is stored in the space on the push member side. Specifically, the first projection may be generally conical, generally truncated conical, generally prismoidal, generally truncated prismoidal, generally columnar, generally spherical or others. The same applies to the second projection.

Further, the shape of the first projection may be related to the outer dimension of the plug, the material from which the plug is made, the medical substance to be filled in the space between the plug and the choked end, etc. With this arrangement, it becomes possible to identify the plug's outer dimension, the material from which the plug is made, the medical substance filled in the space between the plug and the choked end, etc., by a visual observation on the shape of the first projection. Likewise, the second projection may be related to the medical substance filled in the space between the push member and the plug, etc.

It should be noted here that the above-described embodiments covers a case where the barrel 12 is made of synthetic resin. However, the material for the barrel is not limited to this: For example, the barrel may be made of glass.

Further, the above-described embodiments covers a case where the syringe 10 (10*a*) is a two-chamber type which uses one plug 16 (100). However, two or more plugs 16 (100) may be used to provide three or more chambers in the barrel 12.

Further, the medical substance L1 and the medical substance L2 are injected sequentially by the pressure from the side on the open end 18 generated by the sliding movement of the push member 14. Therefore, whichever of the medical substance L1 and the medical substance L2 stored in the syringe according to the present invention may have a higher viscosity than the other.

Still further, the fluids to be stored in the syringe according to the present invention are not limited to liquid, but may be gas. For example, air may be filled in the space between the push member 14 and the plug 16 (100) instead of the medical substance L2. This allows to push out the medical substance L1 remaining in the needle, the connecting tube, etc. connected to the injection portion 20*a* by the air, when the amount of medical substance L1 is small or the medical substance L1 is expensive.

The present invention being thus far described and illustrated in detail, it is obvious that these description and drawings only represent examples of the present invention, and should not be interpreted as limiting the invention. The spirit and scope of the present invention is only limited by words used in the accompanied claims.

The invention claimed is:

1. A multi-chamber syringe comprising:
   a barrel, having a substantially consistent inner shape along the length of the barrel, and having an open end and a choked end, the choked end having an injection hole;
   a push member disposed to fit an inner side surface of the barrel and slidable on the inner side surface; and
   an elastic plug having a substantially columnar main body of a diameter smaller than the inner side surface of the barrel, a flange provided on a side surface of the main body at an end closer to the open end for contacting the inner side surface, and a flange provided on the side surface of the main body at an end closer to the choked end for contacting the inner side surface, the elastic plug being disposed more closely to the choked end than the push member, to fit the inner side surface and slidable on the inner side surface; the plug partitioning an inside space of the barrel into two chambers each capable of storing a fluid;

the syringe further comprising:

a first projection with an eccentric top, provided on a first main surface of the plug, said first main surface facing the choked end of the barrel; and an annular flow path made between the inner side surface of the barrel and a portion of the main body of the plug disposed between the flanges, wherein application of a pressure from an open end side to the plug, with the first projection contacting with the choked end, causes the plug to tilt in the barrel, makes a first gap opening at only a portion of the flange on the open end side, while maintaining contact of the remaining portion of the flange with the inner side surface, and the first gap opening communicating with the flow path, and makes a second gap opening, which is substantially diametrically opposite to the first gap opening in a circumferential direction of the annular flow path, said second gap opening at only a portion of the flange on the choked end side, while maintaining contact of the remaining portion of the flange with the inner side surface, and the second gap opening communicating with the flow path, so as to provide a path for flow of substantially all of a fluid stored between the elastic plug and the push member through the first gap opening, then circumferentially through the annular flow path, and then through the second gap opening.

2. The syringe according to claim 1, wherein the first projection has a slanted surface slanted with respect to the first main surface of the plug on the choked end side, and does not make contact with the inner side surface, the slanted surface being formed with a groove for connecting the second gap opening with the injection hole.

3. The syringe according to claim 2, further comprising a second projection provided on a second main surface of the plug, said second main surface facing the open end of the barrel, the second projection being eccentric in an opposite direction to the first projection, in relation to a plane parallel to the first main surface of the plug, and not making contact with the inner side surface.

* * * * *